(12) United States Patent
Dorval et al.

(10) Patent No.: US 8,309,318 B2
(45) Date of Patent: Nov. 13, 2012

(54) DETECTION OF ANTIGEN SPECIFIC IMMUNOCOMPLEXES

(75) Inventors: Brent Dorval, Hopedale, MA (US); Daniel C. Dantini, Ormond Beach, FL (US)

(73) Assignee: Brendan Bioscience, LLC, Hopedale, MA (US)

( * ) Notice: Subject to any disclaimer, the term of this patent is extended or adjusted under 35 U.S.C. 154(b) by 406 days.

(21) Appl. No.: 11/434,511

(22) Filed: May 16, 2006

(65) Prior Publication Data
US 2006/0275846 A1 Dec. 7, 2006

Related U.S. Application Data

(63) Continuation-in-part of application No. 11/053,680, filed on Feb. 9, 2005, now abandoned.

(60) Provisional application No. 60/542,868, filed on Feb. 10, 2004, provisional application No. 60/681,154, filed on May 16, 2005.

(51) Int. Cl.
*G01N 33/543* (2006.01)
*G01N 33/53* (2006.01)
*G01N 33/564* (2006.01)
*G01N 33/535* (2006.01)
*G01N 33/539* (2006.01)

(52) U.S. Cl. ...... 435/7.94; 435/7.92; 436/507; 436/518; 436/539

(58) Field of Classification Search .............. None
See application file for complete search history.

(56) References Cited

U.S. PATENT DOCUMENTS
5,348,876 A * 9/1994 Michaelsen et al. .......... 435/326

FOREIGN PATENT DOCUMENTS
GB 2 362 211 A * 11/2001

OTHER PUBLICATIONS

Definition of "autoantigen" (2007); In the American, Heritage Medical Dictionary. Retrieved Sep. 1, 2007, from http://www.credoreference.com/entry/6565867.*
Scott et al. "Pathogenesis of Food Protein Intolerance" Acta Pædiatrica vol. 78 Issue s351 (1989), pp. 48-52.*
Host et al. "Cow's milk protein allergy and intolerance in infancy: Some clinical, epidemiological and immunological aspects" Pediatr Allergy Immunol. 1994;5(5 Suppl):1-36.*
Monoclonal antibodies against Complement 3 Neoantigens for Detection of Immune Complexes and Complement Activation, M. Teresa Aguado et al., J. Clin Invest. vol. 76, Oct. 1985, 1418-1426.
Neoantigens in complement component C3 as detected by monoclonal antibodies, Nilsson et al. Biochem J. (1990) 268, 55-61.
Conformational differences between surface-bound and fluid-phase complement-component-C3 fragments, Biochem. J. (1992) 282, 715-721.

* cited by examiner

*Primary Examiner* — Christine Foster
(74) *Attorney, Agent, or Firm* — Timothy H. Van Dyke; Beusse, Wolter, Sanks, Mora & Maire, P.A.

(57) ABSTRACT

The present invention relates to methods and devices for detecting biological entities and components associated with hypersensitivity reactions in patients with allergies, cancer or autoimmune disease. Specifically, the assays of the invention are capable of qualitatively and/or quantitatively detecting allergen specific immunocomplexes by assaying for immobilized C3b in a biological sample produced as a result of exposure to food.

12 Claims, No Drawings

DETECTION OF ANTIGEN SPECIFIC IMMUNOCOMPLEXES

RELATED APPLICATIONS

This application claims priority to U.S. Ser. No. 60/681,154 filed May 16, 2005, which is incorporated by reference in its entirety. This application is a Continuation-in-Part of U.S. Ser. No. 11/053,680, filed Feb. 9, 2005, now abandoned, which claims priority to U.S. Ser. No. 60/542,868 filed Feb. 10, 2004, both of which are incorporated by reference in their entirety.

BACKGROUND OF THE INVENTION

1. Field of the Invention

The present invention relates to methods and devices for detecting biological entities and components associated with hypersensitivity reactions in patients with food allergies, autoimmunity or cancer.

2. Background

It is well established that food-related allergies cause a variety of illnesses, whether it be in humans or other animals. Approximately two percent of adults and about five percent of infants and young children in the United States suffer from food allergies and each year roughly 30,000 individuals require emergency room treatment as a result. At present, there is no cure for food allergies and a food allergic consumer must avoid the food to which the consumer is allergic. The timing and location of an allergic reaction to food is affected by digestion. For example, an allergic person may first experience a severe itching of the tongue or "tingling lips." Vomiting, cramps or diarrhea may follow. Later, as allergens enter the bloodstream and travel throughout the body, they can cause a drop in blood pressure, hives or eczema, or asthma when they reach the lungs. The onset of these symptoms may vary from a few minutes to an hour or two after the food is eaten. Delayed reactions take hours or days to manifest symptoms.

Von Pirquet first described serum sickness, the prototype of Immune Complex disease in 1925. Any food protein entering the circulation in sufficient quantity can produce symptom patterns resembling serum sickness. If antigens make it into the blood stream, they can stimulate the production of antibodies. These antibodies can then combine with antigens in the blood stream to produce circulating immune complexes (CICs).

Food-enriched blood, coming from the gastrointestinal tract (GIT), goes through the liver where most immune-complexes are removed. If circulating complexes pass the liver filter, they may cause disturbances in many organs. The other path of absorption of molecules from the GIT is through lymphatic drainage. The lymph channels flow together to form the thoracic duct, a flimsy vessel which drains its contents into the subclavian vein. This pathway may direct antigenic molecules directly to the lungs where food antigens may excite intrinsic asthmatic attacks, bronchitis, or more serious and enigmatic inflammatory lung diseases.

The combination of antibody with antigen in the blood stream is a circulating immune complex (CIC). In most cases, CICs are simply removed from the circulation by macrophages prior to triggering a cascade of events which may cause multiple symptoms, and possibly tissue damage.

CIC's activate complement which is a circulating system of 25 proteins which interact to produce a variety of defensive molecular weapons. There are two main functions of the complement cascade. The first is to opsonize bacteria, viruses and antibodies with covalently bound C3b. The bacterial, viral or CIC-C3b complex binds to the CR1 receptors through the ligand C3b. CR1 receptors are found on red blood cells or other cells, such as macrophages which result in rapid removal of the C3b-CICs. The CR1 receptor is a cofactor that causes rapid degradation of C3b by Factor H and Factor I to CIC-C3bi and ultimately to CIC-C3d/C3d,g. It is noteworthy that C3d/C3d,g contain a thioester bond, which causes this fragment to remain covalently bound to the activator i.e. CIC, indefinitely. The second function is to lyse cells by activation of the terminal pathway proteins C5 through C9. C5-C9 attach to cell surfaces, assemble into pores (membrane attack complex), and disrupt the cell membrane or cell walls. The net effect is that ions and water flow into a cell causing the cell to burst.

Clearly the inadvertent or inappropriate activation of complement can have serious consequences for healthy self-cells and tissues. CIC's leave capillaries to trigger inflammatory events in target tissues. A classic model of complex-induced pathology is the Arthus reaction, which appears 3-6 hours after antigen challenge and involves large insoluble complexes with complement (C3b) passing through vessel walls to excite inflammatory responses in target tissues.

Regardless of the animal, allergens (antigens) from food, food additives or environmental sources cause an acquired immunity. Acquired immunity is simply the ability of allergens to either cause the production of antibodies (IgM, IgA, IgG, IgE and IgD) or interact with the mucosa or epidermis and stimulate T-cells. These antibodies react with the allergen and cause symptoms associated with allergy. Allergic reactions are classified into four types (I, II, III, IV) based on the Gell/Coombs scheme.

Immunoenzymometric assays involve the binding of an analyte of interest with a reaction or binding partner, where the binding partner carries a label. The binding partner is contained in a test strip, well or other apparatus so that it is non-reactive unless and until its partner analyte contacts the test strip. When this happens, the analyte and labelled binding partner bind to each other, forming a complex. Detection is accomplished by reacting the label carried by the binding partner with another substance, to form a detectable signal. When the label is an enzyme, as it frequently is, the substance is a substrate for the enzyme. The substrate for the enzyme either forms a visible color or changes color. Measuring the change or amount of color provides a measure of the produced complex, and hence of the analyte.

There is a need for quick, accurate, simple assays that can be performed by laboratory personnel as well as by non-technical personnel outside of a laboratory setting to test biological fluids of organisms to determine the presence of biological analytes such as immunoglobulins and immunocomplexes in the blood that are associated with or indicative of food, food additive or chemical allergies; or cancer and autoimmune disease.

All publications, scientific, patent or otherwise, referenced herein are hereby incorporated by reference in their entirety for all purposes.

SUMMARY OF THE INVENTION

One aspect of the invention relates to a kit for determining the presence of antigen-specific immunocomplexes in a biological sample comprising a solid support comprising an immobilized antigen that is to be exposed to the biological sample thereby binding and immobilizing antigen-specific immunocomplexes; and a binding partner that specifically binds the immobilized immunocomplex C3b.

In one embodiment of this aspect of the invention, the biological sample is serum or saliva. In another embodiment, the solid support is a microtiter dish well. In yet another embodiment, the binding partner is an anti-C3d antibody. In still another embodiment, the anti-C3d antibody is detected by a labeled second binding partner that is specific for the anti-C3d antibody. In yet a further embodiment the binding partner is an horseradish peroxidase (HRP) labeled anti-C3d antibody. Still another embodiment comprises a the third binding partner specific for immunoglobulin portion of the immunocomplex C3b. In yet another embodiment, the third binding partner is a human anti-IgG antibody. In still another embodiment, the anti-IgG antibody is detected by a labeled fourth binding partner that is specific for the anti-IgG antibody. In still a further embodiment, the third binding partner is conjugated to HRP. In yet another embodiment, the labeled second binding partner specific for the at least one binding partner is part of a signal producing system. Still another embodiment, the amount of label immobilized on the solid support can be read quantitatively. In still a further embodiment, the antigen is an allergen derived from the group consisting of milk, corn, shrimp, lobster, crab, peanuts, walnuts, fish, eggs, soy and wheat. In still another embodiment, the allergen is selected from the group consisting of monosodium glutamate (MSG), gluten, casein, β-lactoglobulin and bovine serum albumin. In still a further embodiment the antigen is an autoantigen. In another embodiment, the antigen is a tumor antigen.

Another aspect of the invention relates to a method of determining the presence of antigen-specific immunocomplexes in a biological sample comprising exposing a solid support comprising an immobilized antigen to biological sample to render immobilized immunocomplex C3b; washing unbound molecules from the biological samples from the solid support sample; exposing the solid support to at least one binding partner that specifically binds the immobilized immunocomplex C3b; washing unbound labeled binding partner from the solid support; detecting the presence of the at least one binding partner bound to the solid support; and correlating it with the presence of antigen specific immunocomplexes in the biological sample.

In one embodiment of this aspect of the invention, the biological sample is serum or saliva. In another embodiment the solid support is a microtiter dish well. In still another embodiment, the binding partner is an anti-C3d antibody. In still a further embodiment, the anti-C3d antibody is detected by a labeled second binding partner that is specific for the anti-C3d antibody. In yet another embodiment, the binding partner is a horseradish peroxidase (HRP) labeled anti-C3d antibody. In yet a further embodiment, the method further comprises adding a third binding partner specific for immunoglobulin portion of the immobilized immunocomplex C3b. In another embodiment, the third binding partner is a human anti-IgG antibody. In still another embodiment, the anti-IgG antibody is detected by a labeled fourth binding partner that is specific for the anti-IgG antibody. In still another embodiment, the third binding partner is conjugated to HRP. In yet a further embodiment, the presence of the at least one binding partner bound to the solid support is detected by a second labeled binding partner which is part of a signal producing system. In still another embodiment, the amount of label immobilized on the solid support is be read quantitatively. In yet another embodiment, the antigen is an allergen derived from the group consisting of milk, corn, shrimp, lobster, crab, peanuts, walnuts, fish, eggs, soy and wheat. In still another embodiment, the antigen is selected from the group consisting of monosodium glutamate (MSG), gluten, casein, β-lactoglobulin and bovine serum albumin. In still a further embodiment the antigen is an autoantigen. In another embodiment, the antigen is a tumor antigen.

Another aspect of the invention relates to a method of determining whether a patient is allergic to a particular allergen comprising: exposing a solid support comprising the immobilized allergen or analog thereof to a biological sample derived from the patient; washing unbound molecules from said biological sample from said the solid support; exposing the solid support to a binding partner that specifically binds C3b and a binding partner that specifically binds an immunoglobulin portion of an allergen-specific immunocomplex; washing unbound at least one binding partner from said solid support; and detecting the presence of said at least one binding partner remaining bound on the solid support; and correlating the presence of the at least one binding partner on the solid support with the patient being allergic to the allergen.

In one embodiment of this aspect of the invention, the biological sample is serum or saliva. In another embodiment, the solid support is a microtiter dish well. In a further embodiment, the binding partner that specifically binds C3b is an anti-C3d antibody. In yet another embodiment, the binding partner that specifically binds C3b is detected by a labeled binding partner. In yet a further embodiment, the binding partner that specifically binds an immunoglobulin portion of an allergen-specific immunocomplex is detected by a labeled binding partner. In still another embodiment, the amount of label immobilized on the solid support is be read quantitatively. In still a further embodiment, the allergen is derived from the group consisting of milk, corn, shrimp, lobster, crab, peanuts, walnuts, fish, eggs, soy and wheat. In still another embodiment, the allergen is selected from the group consisting of monosodium glutamate (MSG), gluten, casein, β-lactoglobulin and bovine serum albumin.

Another aspect of the invention relates to a kit for determining the presence of allergen specific immunocomplexes in a biological sample comprising, a solid support comprising an immobilized allergen that is to be exposed to the biological sample thereby binding and immobilizing allergen specific immunocomplexes and; and at least one labeled binding partner that specifically binds C3b.

In one embodiment of this aspect of the invention, the biological sample is serum or saliva. In another embodiment, the solid support is a microtiter dish well. In yet another embodiment, the first labeled binding partner is an anti-C3d antibody. In yet another embodiment, the label is part of a signal producing system. In still another embodiment, the amount of label immobilized on the solid support can be read quantitatively. In still a further embodiment the allergen is derived from the group consisting of milk, corn, shrimp, lobster, crab, peanuts, walnuts, fish, eggs, soy and wheat. In yet another embodiment, the allergen is selected from the group consisting of monosodium glutamate (MSG), gluten, casein, β-lactoglobulin and bovine serum albumin.

Another aspect of the invention relates to a method of determining the presence of allergen specific immunocomplexes in a biological sample comprising: exposing a solid support comprising an immobilized allergen to a biological sample; washing unbound molecules from the biological sample from the solid support; exposing the solid support to at least one labeled binding partner that specifically binds C3b; washing unbound labeled binding partners from the solid support; detecting the presence of label bound to the solid support; and correlating it with the presence of allergen specific immunocomplexes in the biological sample.

In one embodiment of this aspect of the invention, the biological sample is serum or saliva. In another embodiment the solid support is a microtiter dish well. In still another embodiment, the labeled binding partner is an anti-C3d antibody. In yet a further embodiment, the label is part of a signal producing system. In still another embodiment the amount of label immobilized on the solid support is be read quantitatively. In yet another embodiment, the allergen is derived from the group consisting of milk, corn, shrimp, lobster, crab, peanuts, walnuts, fish, eggs, soy and wheat. In still another embodiment the allergen is selected from the group consisting of monosodium glutamate (MSG), gluten, casein, β-lactoglobulin and bovine serum albumin.

Another aspect of the invention relates to a test strip apparatus for determining the presence of allergen specific immunocomplexes in a biological sample comprising a bibulous substrate comprising a first zone comprising a diffusible labeled receptor that specifically binds C3b; a second zone comprising at least one area wherein each area has at least one immobilized allergen; and a third zone comprising an immobilized second receptor specific for the diffusible labeled receptor; the zones located in sequence in a capillary fluid flow direction in the test strip apparatus; and wherein an accumulation of label in the second zone correlates with the presence of, and/or is proportional to an amount of allergen specific immunocomplexes in the biological sample.

In one embodiment of this aspect of the invention, the biological sample is serum or saliva. In another embodiment, the bibulous substrate a nitrocellulose membrane. In a further embodiment, the diffusible labeled receptor is anti-C3d antibody. In yet another embodiment, the label comprises latex particles. In still another embodiment, the label comprises colloidal gold particles. In yet a further embodiment, the at least one allergen is derived from the group consisting of milk, corn, shrimp, lobster, crab, peanuts, walnuts, fish, eggs, soy and wheat. In another embodiment the at least one allergen is from the group consisting of monosodium glutamate (MSG), gluten, casein, β-lactoglobulin and bovine serum albumin. In still another embodiment the the second zone comprises a plurality of areas that are stripes of different immobilized allergens. In yet another embodiment, the diffusible labeled receptor of labeled binding partner is gold-conjugated goat anti-human C3d antibody.

In yet a further embodiment the immobilized second receptor specific for the diffusible labeled receptor is a mouse generated anti-goat antibody.

Another aspect of the invention relates to a method of determining the presence of allergen specific immunocomplexes in a biological sample comprising, providing a test strip apparatus comprising a first zone comprising at one diffusible labeled receptor that specifically binds the C3b; a second zone comprising at least one area wherein each area has at least one immobilized allergen; and a third zone comprising an immobilized second receptor specific for the at least one diffusible labeled receptor; located in sequence in a capillary fluid flow direction in the test strip apparatus; and allowing the biological fluid to migrate up the test strip apparatus by capillary action; and reading the test strip by correlating the presence of label accumulation in the second area with the presence of allergen specific immunocomplexes in the biological sample.

In one embodiment of this aspect of the invention, the biological sample is serum or saliva. In another embodiment, the bibulous substrate is a nitrocellulose membrane. In a further embodiment, the labeled binding partner is an anti-immunocomplex C3d antibody. In yet a further embodiment, the label comprises latex particles. In still another embodiment, the label comprises colloidal gold particles. In still another embodiment, the at least one allergen is derived from the group consisting of milk, corn, shrimp, lobster, crab, peanuts, walnuts, fish, eggs, soy and wheat. In still another embodiment, the at least one allergen is derived from the group consisting of monosodium glutamate (MSG), gluten, casein, β-lactoglobulin and bovine serum albumin. In another embodiment, the the second zone comprises a plurality of areas that are strips of immobilized different allergens. In still another embodiment, the diffusible labeled binding partner is gold conjugated goat anti-human C3d antibody. In yet another embodiment, the immobilized second receptor specific for the diffusible labeled receptors is a mouse generated anti-goat antibody.

Another aspect of the invention relates to a method of determining whether a patient is allergic to a particular allergen comprising: exposing a solid support comprising the immobilized allergen or analog thereof to a biological sample; washing unbound molecules from the biological sample from the solid support; exposing the solid support to at least one labeled binding partner that specifically binds C3b; washing unbound labeled binding partners from the solid support; detecting the presence of label bound to the solid support; and correlating it with the presence of allergen specific immunocomplex in the biological sample.

In one embodiment of this aspect of the invention, the biological sample is serum or saliva. In another embodiment the solid support is a microtiter dish well. In still another embodiment, the labeled binding partner is an anti-C3d antibody. In yet a further embodiment, the label is part of a signal producing system. In still another embodiment the amount of label immobilized on the solid support is be read quantitatively. In yet another embodiment, the allergen is derived from the group consisting of milk, corn, shrimp, lobster, crab, peanuts, walnuts, fish, eggs, soy and wheat. In still another embodiment the allergen is selected from the group consisting of monosodium glutamate (MSG), gluten, casein, β-lactoglobulin and bovine serum albumin.

Another aspect of the invention relates to a method of determining whether a patient is allergic to a particular allergen comprising, providing a test strip apparatus comprising a first zone comprising at one diffusible labeled receptor that specifically binds the C3b; a second zone comprising the immobilized allergen or analog thereof; and a third zone comprising an immobilized second receptor specific for the at least one diffusible labeled receptor; located in sequence in a capillary fluid flow direction in the test strip apparatus; and allowing the biological fluid to migrate up the test strip apparatus by capillary action; and reading the test strip by correlating the presence of label accumulation in the second area with the presence of allergen specific immunocomplexes in the biological sample.

In one embodiment of this aspect of the invention, the biological sample is serum or saliva. In another embodiment, the bibulous substrate is a nitrocellulose membrane. In a further embodiment, the labeled binding partner is an anti-immunocomplex C3d antibody. In yet a further embodiment, the label comprises latex particles. In still another embodiment, the label comprises colloidal gold particles. In still another embodiment, the at least one allergen is derived from the group consisting of milk, corn, shrimp, lobster, crab, peanuts, walnuts, fish, eggs, soy and wheat. In still another embodiment, the at least one allergen is derived from the group consisting of monosodium glutamate (MSG), gluten, casein, β-lactoglobulin and bovine serum albumin. In another embodiment, the the second zone comprises a plurality of areas that are strips of immobilized different allergens. In still another embodiment, the diffusible labeled binding partner is gold conjugated goat anti-human C3d antibody. In yet another embodiment, the immobilized second receptor specific for the diffusible labeled receptors is a mouse generated anti-goat antibody.

Another aspect of the invention relates to a kit for determining the presence of allergen-specific immunoglobulins and immunocomplex C3b in a biological sample comprising: a solid support comprising an immobilized allergen that is to be exposed to a biological sample thereby binding and immobilizing allergen-specific immunoglobulins and immunocomplex C3b; and at least two labeled binding partners a first labeled binding partner that specifically binds the immobilized allergen-specific immunoglobulins; and a second labeled binding partner that specifically binds the immobilized immunocomplex C3b (IC-C3b).

In one embodiment of this aspect of the invention the biological sample is serum or saliva. In another embodiment, the solid support is a microtiter dish well. In yet a further embodiment, the first labeled binding partner is selected from the group consisting of labeled anti-human, anti-IgG, anti-IgA, and anti-IgM antibodies and said second labeled binding partner is an anti-C3d antibody. In still another embodiment, the first labeled binding partner is anti-IgG antibody and the second labeled binding partner is an anti-C3d antibody. In another embodiment, the label is part of a signal producing system. In a further embodiment, the amount of label immobilized on the solid support can be read quantitatively. In still another embodiment, the allergen is derived from the group consisting of milk, corn, shrimp, lobster, crab, peanuts, walnuts, fish, eggs, soy and wheat. In yet a further embodiment, the allergen is selected from the group consisting of monosodium glutamate (MSG), gluten, casein, β-lactoglobulin and bovine serum albumin.

Another aspect of the invention relates to a method of determining the presence of allergen-specific immunoglobulins and immunocomplex C3b in a biological sample comprising: exposing a solid support comprising an immobilized allergen to a biological sample; washing unbound molecules from the biological samples from the solid support; exposing said solid support to at least two labeled binding partners: a first labeled binding partner that specifically binds the immobilized allergen-specific immunoglobulins; and a second labeled binding partner that specifically binds the immobilized immunocomplex C3b; washing unbound labeled binding partners from the solid support; detecting the presence of label bound to the solid support; and correlating it with the presence of allergen specific IC-C3b and allergen specific immunoglobulins in the biological sample.

In one embodiment of this aspect of the invention, the biological sample is serum or saliva. In another embodiment, the solid support is a microtiter dish well. In a further embodiment, the first labeled binding partner is selected form the group consisting of labeled anti-human, anti-IgG, anti-IgA, and anti-IgM antibodies and said second labeled binding partner is an anti-C3d antibody. In yet another embodiment, the first labeled binding partner is anti-IgG antibody and said second labeled binding partner is an anti-C3d antibody. In still another embodiment, the label is part of a signal producing system. In yet a further embodiment, the amount of label immobilized on the solid support is be read quantitatively. In another embodiment, the allergen is derived from the group consisting of milk, corn, shrimp, lobster, crab, peanuts, walnuts, fish, eggs, soy and wheat. In yet a further embodiment, the allergen is selected from the group consisting of monosodium glutamate (MSG), gluten, casein, β-lactoglobulin and bovine serum albumin.

Another aspect of the invention relates to a test strip apparatus for determining the presence of allergen-specific immunoglobulins and immunocomplex C3b in a biological sample comprising a bibulous substrate comprising a first zone comprising at least two diffusible labeled receptors: a first diffusible labeled receptor that specifically binds the allergen-specific IgE, IgG, IgA and/or IgM; and a second diffusible labeled receptor that specifically binds C3b; a second zone comprising at least one area wherein each area has at least one immobilized allergen; and a third zone comprising an immobilized second receptor specific for said first and/or said second diffusible labeled receptor; located in sequence in a capillary fluid flow direction in said test strip apparatus; and wherein an accumulation of label in the second zone correlates with the presence of, and is proportional to an amount of allergen specific IC-C3b and allergen specific immunoglobulins in the biological sample.

In one embodiment of this aspect of the invention, the biological sample is serum or saliva. In another embodiment, the bibulous substrate a nitrocellulose membrane. In a further embodiment, the first diffusible labeled receptor is labeled anti-IgG antibody and said second diffusible labeled receptor is anti-C3d antibody. In yet another embodiment, the label comprises latex particles. In a further embodiment, the label comprises colloidal gold particles. In still another embodiment, the at least one allergen is derived from the group consisting of milk, corn, shrimp, lobster, crab, peanuts, walnuts, fish, eggs, soy and wheat. In yet another embodiment, the at least one allergen is selected from the group consisting of monosodium glutamate (MSG), gluten, casein, β-lactoglobulin and bovine serum albumin. In still another embodiment, the second zone comprises a plurality of areas that are stripes of different immobilized allergens. In a further embodiment, the first diffusible labeled receptor of labeled binding partner is gold-conjugated goat anti-human IgG antibody and said second diffusible labeled receptor is gold-conjugated goat anti-human C3d antibody. In a another embodiment, the immobilized second receptor specific for the diffusible labeled receptors is a mouse generated anti-goat antibody.

Another aspect of the invention relates to a method of determining the presence of allergen-specific immunoglobulins and immunocomplex C3b in a biological sample comprising: a first zone comprising at least two diffusible labeled receptors: a first diffusible labeled receptor that specifically binds the allergen-specific IgE, IgG, IgA and/or IgM; and a second diffusible labeled receptor that specifically binds C3b; a second zone comprising at least one area wherein each area has at least one immobilized allergen; and a third zone comprising an immobilized second receptor specific for said first and/or said second diffusible labeled receptor; located in sequence in a capillary fluid flow direction in said test strip apparatus; and allowing said biological fluid to migrate up the test strip apparatus by capillary action; and reading said test strip by correlating the presence of label accumulation in said second area with the presence of allergen specific IC-C3b and allergen specific immunoglobulins in the biological sample.

In one embodiment, the biological sample is serum or saliva. In another embodiment, said bibulous substrate a nitrocellulose membrane. In a further embodiment, the at least two labeled binding partners are labeled anti-IgG antibodies and anti-immunocomplex C3d antibodies. In still another embodiment, the label comprises latex particles. In yet another embodiment, the label comprises colloidal gold particles. In still a further embodiment, the at least one allergen is derived from the group consisting of milk, corn, shrimp, lobster, crab, peanuts, walnuts, fish, eggs, soy and wheat. In another embodiment, the at least one allergen is selected from the group consisting of monosodium glutamate (MSG), gluten, casein, β-lactoglobulin and bovine serum albumin. In a further embodiment, the second zone comprises a plurality of areas that are strips of immobilized different allergens. In still a further embodiment, the first labeled binding partner is gold conjugated goat anti-human IgG antibody and said second diffusible labeled receptor is gold-conjugated goat anti-human C3d antibody. In yet another embodiment, the immobilized second receptor specific for the diffusible labeled receptors is a mouse generated anti-goat antibody.

Another aspect of the invention relates to using the method and devices described herein to diagnose hypersensitivity reactions wherein wherein a presence of allergen-specific IgE and a substantial lack of allergen-specific IgG, IgA, IgM and IC-C3b in the biological sample correlates with Type I hypersensitivity reactions; a presence of allergen-specific IgG, IgA, and IgM and IC-C3b and a substantial lack of allergen-specific IgE in the biological sample correlates with Type II hypersensitivity reactions; a presence of allergen-specific IgG and IC-C3b and a substantial lack of allergen-specific IgE, IgA, IgM in the biological sample correlates with Type I hypersensitivity reactions; and a substantial lack of allergen-specific IgG, IgA, IgM and IC-C3b in the biological sample correlates with Type I hypersensitivity reactions.

DETAILED DESCRIPTION OF THE INVENTION

The invention relates to methods, kits and apparatuses for the detection and determination of antibodies and/or immune complexes that bind to antigens, e.g., allergens in foods, chemicals, and food additives; tumor antigens or autoantigens. Particularly, the inventors have discovered that antigen-specific ICs in a biological fluid can be detected by detecting C3b and preferably by the presence of the C3d portion of C3b. Additionally, the amount of C3b detected correlates with the amount of antigen specific immunocomplexes in a biological sample. The presence of antigen specific immunocomplexes in a biological sample indicate that the patient from which the sample is derived is mounting an immune reaction to that allergen. If the antigen is an allergen then the patient may be allergic to that antigen. If the antigen is an tumor antigen then the patient may have a tumor expressing that antigen. If the antigen is an autoantigen, the patient may have an autoimmune disease.

"Antigen" as used herein refers to a substance that stimulates an immune response, especially the production of antibodies. Antigens are usually proteins or polysaccharides, but can be any type of molecule, including small molecules (haptens) coupled to a carrier-protein.

Exogenous antigens such as allergens, are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4+) by the use of class II histocompatibility molecules on their surface. Some T cells are specific for the peptide:MHC complex. They become activated and start to secrete cytokines. Cytokines are substances that can activate cytotoxic T lymphocytes (CTL), antibody-secreting B cells, macrophages and other cells.

Endogenous antigens are antigens that have been generated within the cell, as a result of normal cell metabolism, or viral or intracellular bacterial infection. The fragments are then presented on the cell surface in the complex with class I histocompatibility molecules. If activated cytotoxic CD8+ T cells recognize them, the T cells begin to secrete different toxins that cause the lysis or apoptosis of the infected cell. In order to keep the cytotoxic cells from killing cells just for presenting self-proteins, self-reactive T cells are deleted from the repertoire as a result of central tolerance (also known as negative selection which occurs in the thymus). Only those CTL that do not react to self-peptides that are presented in the thymus in the context of MHC class I molecules are allowed to enter the bloodstream.

Autoimmunity is the failure of an organism to recognize its own constituent parts (down to the sub-molecular levels) as "Self", which results in an immune response against its own cells and tissues. Any disease that results from such an aberrant immune response is termed an autoimmune disease, the prominent examples being Systemic Lupus Erythematosus (SLE), Sjögren's syndrome and Rheumatoid Arthritis (RA). An autoantigen is usually a normal protein or complex of proteins (and sometimes DNA or RNA) that is recognized by the immune system of patients suffering from a specific autoimmune disease. These antigens should under normal conditions not be the target of the immune system, but due to mainly genetic and environmental factors the normal immunological tolerance for such an antigen has been lost in these patients.

Tumor antigens are those antigens that are presented by the MHC I molecules on the surface of tumor cells. These antigens can sometimes be presented only by tumor cells and never by the normal ones. In this case, they are called tumor-specific antigens and typically result from a tumor specific mutation. More common are antigens that are presented by tumor cells and normal cells, and they are called tumor-associated antigens. Cytotoxic T lymphocytes that recognized these antigens may be able to destroy the tumor cells before they proliferate or metastasize.

"Allergens," as used herein, relate to antigens that cause allergies. Allergens may be from food, chemicals or food additives. Structurally speaking, allergens may range in size from small and simple chemical compounds to polypeptides and other biological macromolecules. Food allergens are commonly found in e.g., Apple, Corn, Oat, Soybean, Baker's Yeast, Cottonseed, Onion, Strawberry, Banana, Cow's Milk, Orange, Sunflower Seed, Beef, English Walnut, Peanut, Tea, Beet, Garlic, Pork, Tomato, Brewer's Yeast, Grapefruit, Red Pepper, Tuna, Broccoli, Green Olive, Rice, Turkey, Cocao, Hops, Rye, White Potato, Cocoanut, Lemon, Safflower Seed, White Seedless Grape, Coffee, Mushroom, Sesame, Whole Egg (Chicken), Cola Nut, Mustard, Sole, Whole Wheat, Almond, Cherry Green Pea, Pineapple, Apricot, Chicken, Honeydew Melon, Pinto Bean, Barley, Chili Pepper, Lamb, Pumpkin, Basil, Cinnamon, Lettuce, Salmon, Beet, Clam, Lima Bean, Scallops, Cabbage, Crab, Lobster, Shrimp, Cantaloupe, Cranberry, Millet, Squash Mix, Carrot, Cucumber, Oregano, Sweet Potato, Cashew Nut, Dill Seed, Peach, Tumeric, Cauliflower, Ginger, Pear, Vanilla, Celery, Green Bean, Pecan, and Watermelon. Common food additives such as monosodium glutamate (MSG) and gluten are also known to be allergens. Children typically outgrow their allergies to milk, egg, soy and wheat, while allergies to peanuts, tree nuts, fish and shrimp usually are not outgrown. Exemplary milk associated allergens are casein, β-lactoglobulin and bovine serum albumin. Panels of the aforementioned allergens are readily available from sources such as Brendan BioScience, LLC (Boston, Mass.)

The information gleaned from using the devices and methods of the invention will allow the clinician to arrive at conclusions with respect to a patient's previous hypersensitivity reaction or their susceptibility to further reactions. According to the Gell/Combs classification, there are four types of hypersensitivity reactions which contain all accepted immune reactions causing human and animal sensitivity to antigens:

Type I, is antibody-mediated (IgE) and is commonly called immediate hypersensitivity because the allergic reaction occurs in less than two hours post allergen exposure. IgE circulates in blood as a free molecule or bound to mast cells and basophils in tissue with a half-life of about two days or two weeks, respectively. When cell-bound IgE binds the allergen, a cascade of events occurs that ultimately leads to (rapid) release of vasoactive mediators, e.g., histamine, that result in clinical symptoms related to allergy. Cell-bound IgE is detected by skin testing, whereas circulating (free) IgE is measured in serum or plasma.

Type II, is also antibody-mediated (IgG, IgM, IgA) and is commonly called delayed hypersensitivity (DTH) because the allergic reaction occurs up to several days post allergen exposure. Type II hypersensitivity occurs when antibody binds to either self-antigen or foreign antigen on cells, and leads to phagocytosis, killer cell activity or complement-mediated lysis. Since IgM is not produced after sensitization, IgG and IgA are the primary mediators of Type II DTH reactions. These antibodies, alone or in combination, bind to either self or foreign antigen on cells (opsonization) leading to phagocytosis, killer cell activity or complement-mediated lysis. IgG activates complement (C3b) leading to formation of the membrane-attack-complex and cell lysis, whereas IgA does not activate complement and is not involved in cell lysis. The type of sample used to measure these antibodies e.g., serum vs. saliva, is very important. For example, after submucosal allergen exposure both IgG and IgA are found in blood, whereas only mucosal IgA is produced in secretory secretions such as saliva. However, topical or intraepithelial exposure to allergens results in secretory IgA in the absence of appreciable IgA or IgG in blood. Based on this, one may want to test for IgA in saliva and gut mucosa, as well as, IgG and IgA in serum if there is a history of exposure to ingested allergens, for example. Recent data shows that IgG binds to mast cells with a half-life of about 3 months. Further, when an allergen binds to IgG on mast cells an "IgE-like" release of vasoactive mediators occurs.

Type III, is antibody-mediated (IgG) and is also a delayed hypersensitivity (DTH) because the allergic reaction occurs days to weeks post allergen exposure. Type III hypersensitivity develops when immune complexes (IC) are formed in large quantities, or cannot be cleared adequately by the reticuloendothelial system. Allergen exposure results in production of IgG, which in turn binds to the allergen forming immune complexes (IC) in blood. IC activate complement resulting in covalent binding of C3b to IgG forming IC-C3b. IC-C3b binds to CR1 receptors on red blood cells (RBC). The RBCc release the IC-C3b in the liver and spleen and the IC-C3b are degraded. If IC are not cleared by RBC, IC deposit at various sites throughout the body. Damage ensues when IC deposit at a site, activate complement and release C3a. C3a causes leucocytes and mast cells to release proteases and vasoactive amines that damage blood vessels or other tissue components.

Type IV, is an entirely cell-mediated form of delayed hypersensitivity (DTH) as the allergic reaction occurs days to weeks post allergen exposure. The most serious DTH is Granulomatous, which occurs when macrophages (MΦ) ingest, but cannot degrade, an allergen resulting in persistent MΦ stimulation. Stimulated MΦ elaborate cytokines that cause the MΦ itself or other cell types to form granulomas. T cells are then stimulated by cytokines, which mediate the range of inflammation responses. There are four types of cell-mediated DTH reactions depending on the type of allergen, route of contact or ability to degrade an allergen. Clinically, the most relevant DTHs are Contact (epidermis) and Granulomatous (mucosa). Contact DTH occurs when a small molecule binds to skin proteins and activates T-cells. The T-cells release cytokines that make skin cells form a typical eczematous rash. For example, latex (medical gloves), nickel (jewelry) or urushiol (Poison Ivy) are small molecules that induce contact DTH. Irrespective of the cell type forming the lesion, T-cells play a major role. Type IV-DTH is diagnosed by exposing the skin or mucosa to allergenic challenge followed by visual exam of redness, swelling and induration.

"Immune- or Immunocomplexes (ICs)" as used herein refer to the aggregations of antibodies with antigen. ICs trigger the activation of the complement cascade. The mammalian complement system is a critical host defense mechanism comprising more than 25 proteins and cellular receptors. Red blood cells intercept complement associated ICs (e.g., IC-C3b) in the bloodstream and safely transport it to the liver.

The complement system is composed of more than 25 different proteins produced by different tissues and cells including hepatocytes, macrophages and gut epithelial cells. These proteins are activated by a variety of agents and their activation proceeds in a cascade fashion leading to pathogen lysis. Gell-Coombs Class II and III reactions are mediated through the Classical (C1), Alternative (C3) and Lytic (C5-C9) complement pathways.

The classical pathway normally requires a suitable antibody (Ab, usually IgG) bound to antigen (Ag), complement components 1, 4, 2 and 3 and Ca++ and Mg++ cations. Binding of C1qrs (a calcium-dependent complex), present in normal serum, to Ag-Ab complexes results in autocatalysis of C1r. The altered C1r cleaves C1s and this cleaved C1s becomes an enzyme (C4-C2 convertase) capable of cleaving both C4 and C2. Activated C1s enzymatically cleaves C4 into C4a and C4b. C4b binds to the Ag-bearing particle or cell membrane while C4a remains a biologically active peptide at the reaction site. C4b binds C2 which becomes susceptible to C1s and is cleaved into C2a and C2b. C2a remains complexed with C4b whereas C2b is released in the micro environment. C4b2a complex, is known as C3 convertase in which C2a is the enzymatic moiety. C3 convertase, in the presence of Mg++, cleaves C3 into C3a and C3b. C3b binds to the membrane to form C4b2a3b complex whereas C3a remains in the micro environment. C4b2a3b complex functions as C5 convertase which cleaves C5 into C5a and C5b. Generation of C5 convertase marks the end of the classical pathway.

The alternative pathway begins with the activation of C3 and requires Factors B and D and $Mg^{++}$ cation, all present in normal serum. A metastable C3b-like molecule (C3i) is generated by slow hydrolysis of the native C3. C3i binds factor B which is cleaved by Factor D to produce C3iBb. C3iBb complex cleaves native C3 into C3a and C3b. C3b binds factor B, which is again cleaved by Factor D to produce C3bBb (C3 convertase). This C3 convertase (or the one generated by classical pathway: C4b2a), if not inactivated, will continue to act on C3 and cause its total depletion.

C3b, in fluid phase, is very short lived unless it finds a suitable stabilizing membrane or molecule (C3 activator). In the absence of exogenous pathogen, it binds quickly to autologous red cells via the C3b receptor, CR1 at a site close to decay accelerating factor (DAF) which prevents the binding of Factor B. Binding to CR1 also makes C3b susceptible to Factor I which cleaves it into many fragments (iC3b, C3c, C3d, C3e, etc.). C4b, generated in the classical pathway, is also regulated by DAF, CR1 and Factor I. A defect in or deficiency of DAF can lead to cell lysis and anemia, as in its absence further activation of C will proceed and lead to the membrane attack pathway (see below) and cell lysis.

Another serum protein, factor H, can displace factor B and bind to C3b. Binding of factor H makes C3b more susceptible to factor I. C3 convertase generated by the classical pathway is regulated also in a similar manner by DAF, Cr1 and Factor I. The only difference is that C4b-binding protein (C4b-BP, not factor H) makes it susceptible to Factor I. A genetic deficiency of factor I (or factor H) leads to uncontrolled C3 activation and is a major cause of inherited C3 deficiency.

Certain bacteria or their products (peptidoglycan, polysaccharides, etc.), provide a protected (activator) surface for C3b. Thus, C3b bound to such a surface is relatively resistant to the action of factor I. Even membrane bound C3bBb dissociates fairly rapidly. Stabilized C3 convertase cleaves more C3 and produces C3bBbC3b complex (analogous to C4b2a3b of the classical pathway), the C5 convertase which cleaves C5 into C5a and C5b. C5b initiates the membrane attack pathway which leads to cell lysis. While these pathways of C3 activation are initiated by different mechanisms, they are analogous to each other and both can lead to membrane lysis.

The alternative pathway provides a means of non-specific resistance against infection without the participation of antibodies and hence provides a first line of defense against a number of infectious agents. Many gram negative and some gram positive bacteria, certain viruses, parasites, heterologous red cells, aggregated immunoglobulins (particularly, IgA) and some other proteins (e.g. proteases, clotting pathway products) can activate the alternative pathway.

The lytic (membrane attack) pathway involves the C5-9 components. C5 convertase generated by the classical or alternative pathway cleaves C5 into C5a and C5b. C5b binds C6 and subsequently C7 to yield a hydrophobic C5b67 complex which attaches quickly to the plasma membrane. Subsequently, C8 binds to this complex and causes the insertion of several C9 molecules to bind to this complex and lead to formation of a hole in the membrane, resulting in cell lysis. The lysis of target cell by C5b6789 complex is nonenzymatic and is believed to be due to a physical change in the plasma membrane. C5b67 can bind indiscriminately to any cell membrane leading to cell lysis. Such an indiscriminate damage to by-standing cells is prevented by protein S (vitronectin) which binds to C5b67 complex and blocks its indiscriminate binding to cells other than the primary target.

An immune complex (IC-C3b) is "complement (C3b) incorporated into the lattice formed during the combination of antibody with soluble antigen", Ratnoff et al., (1983) Springer Semin Immunopathol 6:361-371. The largest IC are formed from multivalent antigens and, in general, large IC activate complement at a higher "rate" than relatively small IC. The actual formation of IC occurs when immunoglobulin (Ig) binds to an antigen (Ag) and subsequently activates the complement cascade. The net result is that C3b covalently binds to the Ig in the "lattice" forming $[Ig]_n[C3b]_n[Ag]_n$. Where $[Ig]_n$ equals multiple antibodies of either IgG or IgM class; $[C3b]_n$ equals multiple molecules of C3b incorporated into the lattice through covalent binding to the Ig; and $[Ag]_n$ equals multiple "copies" of a given antigen incorporated into the lattice through the "Complementarity Determining Region" (CDR) of the Ig. Roitt et al. (eds) 1985 Immunology, CV Mosby Co., Grower Medical Publishing, Toronto, Canada.

C3b can be present in multiple immune complexes that differ with respect to their components. For example, heterogeneous IC can relate to: 1) IC comprised of different amounts (ratios) of the components Ig, Ag and C3b and/or 2) IC of different "sizes". IC produced against a given antigen are comprised of the same components albeit the ratio of the components may differ along with the actual size of the IC. Thus, the IC can be "heterogeneous" because the ratio of Ig:C3b:Ag may differ depending on whether the antibody or antigen is in excess or at equivalence and the valency of the Ag itself. Roitt R (ed) Essential immunology ($3^{rd}$ ed)(1977), Blackwell Scientific Publications, Oxford. For example, IC formed in the presence of Ig or Ag excess will tend to be "small". If the Ig is in excess compared to Ag the Ig:Ag ratio approaches the valency of the antigen. For example, if Ig is in excess over Ag and the Ag has four possible epitopes, the Ig:Ag ratio in the IC will approach the valency of the Ag, i.e. $[Ig]_4:[Ag]_1$. By comparison, IC formed when Ag is in excess over Ig, the ratio of Ig:Ag in the IC approaches the valence of the antibody (two) i.e. $[Ig]_2:[Ag]_1$. In both of the latter cases the IC tend to be small in size. However, IC formed at "equivalence" i.e. Ig and Ag are approximately equal in concentration, will tend to be large i.e. $[Ig]_{40}:[Ag]_{10}$. Since C3b binds to Ig, the proportion of C3b in the IC increases as Ig increases until solubilization (disassociation) of the IC lattice occurs. Thus, the ratios of the components that comprise the IC-C3b vary along with the IC size. That IC's are heterogeneous is true for the reasons listed above but the fact that IC are heterogeneous is irrelevant from the perspective of detection for purposes of this invention because IC-C3b (heterogeneous or homogenous) are detected by the assay in the present patent if the Ig in the IC-C3b is directed against the antigen, e.g., an allergen coated on an ELISA plate. The detection of the invention is therefore, independent of IC-C3b composition (ratio) or size.

The methods and kits disclosed herein envisage preferably measuring and/or detecting IC-C3b via the C3d portion of C3b using for example, an anti-C3d-HRP conjugate. The C3b covalently bound to the Ig in the IC is degraded by serum protease (Factor I) into C3d and C3c. Pangburn et al., (1984) Springer Semin Immunopathol 7:163-192; Nydegger et al., (1983) Springer Semin Immunopathol 6:373-398. However, only C3d remains covalently bound to the IC whereas, C3c is released from the IC into the fluid phase of serum. Thus, if one were to measure IC via the C3c portion of C3b, the IC-C3d would remain undetected because the C3c portion of C3b has been released from the IC-C3b prior to assay because the C3c portion of C3b is not covalently bound to the Ig in the IC lattice. The methods and kits disclosed herein envisage also measuring IgG (heavy chain) along with IC-C3b by preferably by using anti-human-IgG-HRP mixed with anti-C3d-HRP. The inventors have also discovered that by using an additional conjugate, anti-human-IgG-HRP that the signal is additive to that of anti-C3d-HRP.

If a patient is C3b positive, ICs are not being cleared. This is indicative of allergy, cancer or autoimmunity, for example, depending on the antigen used to detect the ICs not being cleared. The inventor has discovered that the clinician can make diagnoses on the basis of an identification and/or quantification of circulating C3b and that the amount of C3b correlates with the amount of antigen specific immunocomplex in a biological sample. Specifically, if a patient's bodily fluid if C3b positive, it indicates the presence of stabilized C3b. C3b can be stabilized by antigen specific immunocomplexes. The invention seeks to detect such antigen specific immunocomplexes by capturing them with immobilized versions of those same antigen. Once immobilized, they may be detected using a labeled binding partner such as a labeled antibody, specific for C3b. It is important to note that the C3b protein can be cleaved into C3d and C3c subunits. Therefore, the invention envisages the detection of IC-C3b either directly, e.g. by an antibody that binds C3b or more preferably, by an antibody that specifically binds the C3d portion of C3b.

As stated above, C3b is usually promptly cleared from the serum if it is not associated with a stabilizing molecule. The inventors note that the presence of serum ICs associated with C3b, is indicative of Class II and III allergic reactions. Because IC-C3b is the common junction for all three complement pathways, it enables measurement of immune reactions that would be missed if one measures antibody levels alone. Accordingly, the invention measures bound C3b (IC-C3b) through its binding to antigen, e.g., autoantigens, tumor antigens or allergens in foods, chemicals, and food additives. For example, if a patient is suspected of being allergic to a particular antigen, that antigen can be immobilized on a solid support, exposed to the patient's biological fluids and the solid support probed for the presence of C3b.

The assays of the invention are capable of estimating the amount of antigen specific immunocomplex by detecting immunocomplexed C3b (IC-C3b) produced as a result of exposure to a particular antigen e.g. an allergen in food, food additives, and chemicals. The devices and methods of the invention can be carried out in various combinations. For example, they can be used to determine the total amount of antigen specific immunocomplex present in a biological sample and correlate the amount with the severity of hypersensitivity, for example. Alternatively, if the source of the hypersensitivity is not known, the inventive assays can quickly be adapted to screen a wide range of antigens such as allergens, autoimmune antigens or tumor antigens.

Preferably, the assaying of antigen specific immunocomplexes by C3b detection is carried out using an immunoassay. Most preferably, the invention measures allergen-specific immunocomplexes by way of detecting IC-C3b produced as a result of exposure to food antigens using ELISA or dipsticks. The immunoassay may be a competitive immunoassay or non-competitive sandwich-type assay. Additionally, the assay may be carried out in a wet or "dry chemistry" solid-state format.

One aspect of the invention utilizes Enzyme-Linked Immunosorbent Assay (ELISA) methodology. Generalized ELISA procedures are well known in the art and can readily be adapted to test for the presence of antigen specific immunocomplexes. Preferably, a biological sample, e.g., serum, suspected of containing antigen specific immunocomplexes is applied to the solid phase upon which an antigen is immobilized. Following a brief period of incubation, the solid phase is rinsed and at least one binding partner is added that specifically binds IC-C3b, thereby forming a sandwich. Preferably, the binding partner is anti-C3d. The label intensity reflects the amount of tested antigen specific immunocomplexes and IC-C3b present in the biological sample.

The binding partner that specifically binds IC-C3b can be labeled either directly detected or indirectly detected by way of an additional labeled secondary binding partner. Any appropriate label which may be directly or indirectly visualized may be utilized in these detection assays including, without limitation, any radioactive, fluorescent, chromogenic (e.g., alkaline phosphatase or horseradish peroxidase), or chemiluminescent label, or a hapten (e.g., digoxigenin or biotin) which may be visualized using a labeled, hapten-specific antibody or other binding partner (e.g., avidin). Exemplary immunoassays are described, e.g., in Ausubel et al., supra, Harlow and Lane, Antibodies: A Laboratory Approach, Cold Spring Harbor Laboratory, New York (1988), and Moynagh and Schimmel, Nature 400:105, 1999. Such labels are also referred to as signal producing systems.

In one specific embodiment, an ELISA is structured such that a series of antigens are screened. For example, allergens derived from Apple, Corn, Oat, Soybean, Baker's Yeast, Cottonseed, Onion, Strawberry, Banana, Cow's Milk, Orange, Sunflower Seed, Beef, English Walnut, Peanut, Tea, Beet, Garlic, Pork, Tomato, Brewer's Yeast, Grapefruit, Red Pepper, Tuna, Broccoli, Green Olive, Rice, Turkey, Cocao, Hops, Rye, White Potato, Cocoanut, Lemon, Safflower Seed, White Seedless Grape, Coffee, Mushroom, Sesame, Whole Egg (Chicken), Cola Nut, Mustard, Sole, Whole Wheat, Almond, Cherry Green Pea, Pineapple, Apricot, Chicken, Honeydew Melon, Pinto Bean, Barley, Chili Pepper, Lamb, Pumpkin, Basil, Cinnamon, Lettuce, Salmon, Beet, Clam, Lima Bean, Scallops, Cabbage, Crab, Lobster, Shrimp, Cantaloupe, Cranberry, Millet, Squash Mix, Carrot, Cucumber, Oregano, Sweet Potato, Cashew Nut, Dill Seed, Peach, Tumeric, Cauliflower, Ginger, Pear, Vanilla, Celery, Green Bean, Pecan, and Watermelon are immobilized. A biological sample, suspected of containing antigen, e.g., allergen, specific immunocomplex is applied to the solid phase. Following a brief period of incubation, the solid phase is rinsed and anti-C3d binding partners are added that will specifically bind any immunoglobulin associated with C3d, respectively, thereby forming a sandwich. Following a second rinsing, the amount of anti-C3d binding partners bound to the solid state is determined and is proportional to the amount of allergen specific immunocomplex present in the biological sample.

If there are no antigen specific immunocomplex present in the biological sample, then substantially no label will be immobilized on the solid phase and will be washed away.

As used herein, "substantially no" refers to almost no detectable antigen specific immunocomplex relative to an amount of strongly detectable antigen specific immunocomplex. For example, the presence of a "background" level of label development would be considered by the skilled artisan to constitute substantially no antigen specific immunocomplex present in the biological sample. Additionally, the amount of immobilized label associated with detectable antigen specific immunocomplex will be about 10 times, preferably about 100 times or more preferably about 1000 times more intense than immobilized label associated with "substantially no" immunocomplex.

Another aspect of the invention relates to an immunoassay carried out on a solid support, e.g., a dipstick. Preferably, the solid support is made of a bibulous material such as nitrocellulose, for example, through which a biological fluid can migrate by capillary action. The bibulous material can be a single structure such as a sheet cut into strips or it can be particulate material bound to a support or solid surface such as found, for example, in thin-layer chromatography. The support for the bibulous material, where a support is desired or necessary will normally be water insoluble, non-porous, and rigid and usually will be of the same length and width as the bibulous strip but may be larger or smaller. A wide variety of organic and inorganic materials, both natural and synthetic, and combinations thereof, may be employed provided only that the support does not interfere with the capillary action of the strip, or non-specifically bind assay components, or interfere with the signal producing system. Illustrative polymers include polyethylene, polypropylene, poly(4-methylbutene), polystyrene, polymethacrylate, poly(ethylene terephthalate), nylon, poly(vinyl butyrate), glass, ceramics, metals, and the like.

Preferably, the dipstick has three zones: a first mobilizable zone, a second trap zone and a third zone arranged so that the first mobilization zone and the third zone are spaced apart by the second trap zone. Basic immunoassay test strip systems are disclosed in U.S. Pat. Nos. 6,001,658; 4,540,659; 4,740,468; 5,451,504 and as well as U.S. Pat. No. 4,956,275; European Patent Application 0 267 066; European Patent Application 0 381 173; U.S. Pat. Nos. 4,959,307; 4,960,691; 4,968,604; 4,952,520; PCT 87/02774; U.S. Pat. Nos. 4,963,468; 4,981,786; European Patent Application 0 383 619; U.S. Pat. Nos. 4,313,734; 4,373,932; 4,956,302; 4,624,929; 3,884,641; 4,965,047; 4,770,853; 5,256,372; 4,857,453; 5,145,789; 4,980,298; 3,399,204; 3,420,205; 4,066,646; 5,120,643; 4,447,192; European Patent Application 0 349 295; European Patent Application 0 306 772; European Patent Application 0 299 428; PCT Application 93/03175; European Patent Application 0 291 194; European Patent Application 0 271 204; and European Patent Application 0 323 605. The test strip may be configured in any appropriate fashion, for any appropriate test, to include alternatives of any one or more of the above-described variants. A detailed discussion of these many variants for suitable test strips appears in the above listed documents, the entire contents of which are hereby fully incorporated by reference. Optionally, the solid support device may be inserted into a holder, such as disclosed in U.S. patent application Ser. No. 08/476,036 to MacKay et al., filed Jun. 7, 1995, whose contents are fully and totally incorporated herein by reference.

A preferred non-competitive test strip immunoassay embodiment provides for moving a biological sample suspected of containing an antigen specific immunocomplex through a first mobilization zone, a second trap zone, and a third detection zone. A diffusible labeled receptor specific for C3b or more preferably the C3d portion of C3b, is provided on the first zone. The second zone has at least one area having at least one immobilized antigen and the third zone provides for a control as it contains an immobilized second receptor specific for the diffusible labeled receptor types. When the dipstick is brought into contact with a biological sample such as serum, the liquid first flows through the first zone mobilizing the diffusible labeled receptors specific to C3b (or C3d portion of C3b).

Once mobilized, the diffusible labeled receptors will bind any C3b (or C3d portion of C3b) present in the biological sample to form a mobile labeled complex. The mobile labeled complex will in turn bind the at least one immobilized antigen located in the second zone to form an immobilized sandwich that can be visualized by the label. The remainder of unbound diffusible labeled receptors continues to migrate to the third control zone where an immobilized second receptor specifically binds and immobilizes some of the diffusible labeled receptors. Label development at the control zone demonstrates that fluid has properly migrated through the dipstick.

If there is substantially no antigen specific immunocomplex present in the biological sample, there will be no immobilization of the diffusible labeled receptors and substantially no label at the second trap zone. Therefore, a negative result will result in label only accumulating at the control zone. Accordingly, it should be clear to one of skill in the art that the amount of label at the second zone is proportional to the amount of antigen specific immunocomplex present in the sample.

In the preferred embodiment, the first zone contains anti-C3b antibodies. Most preferably, there diffusible labeled receptors are gold-conjugated goat anti-human C3d antibody. For this embodiment, the preferred immobilized second receptor specific for the diffusible labeled receptors at the third zone is a mouse generated anti-goat antibody.

Furthermore, the preferred immobilized antigen at the second trap zone is a food derived allergen. Even more preferable is the subdivision of the second zone into discrete areas, such as stripes, each having a different allergen immobilized thereon. This enables the technician to discern among multiple allergen specific immunocomplexes in the biological sample and help the clinician quickly narrow down which allergen and, by extension, which food product or additive, is causing a patient's hypersensitivity response.

Preferably, the first diffusible labeled receptor is an antibody that is labeled with either enzymes, fluorophores, chromophores, radioisotopes, dyes, colloidal pigments or gold, latex particles, or chemiluminescent agents.

In all embodiments of the invention, the label may be directly visible, such as by the use of colloidal particles, e.g. gold and pigments, or latex microparticles. Alternatively, the label may be part of a signal producing system. The signal producing system may have one or more components, at least one component being the label conjugated to an receptor. The signal producing system includes all of the reagents required to produce a measurable signal. Other components of the developer include substrates, coenzymes, enhancers, second enzymes, activators, cofactors, inhibitors, scavengers, metal ions, specific binding substances required for binding of signal generating substances, and the like. The components of the signal producing system may be bound to the strip such as coenzymes, substances that react with enzymatic products, other enzymes and catalysts, and the like. The signal producing system provides a signal detectable by external means, normally by measurement of electromagnetic radiation, desirably by visual examination. For the most part, the signal producing system includes a chromophoric substrate and enzyme, where chromophoric substrates are enzymatically converted to dyes which absorb light in the ultraviolet or visible region, phosphors or fluorophores.

The skilled artisan will also appreciate that the invention may readily be adapted for use on non-human animals, particularly domesticated animals.

In this disclosure there are described only the preferred embodiments of the invention and but a few examples of its versatility. It is to be understood that the invention is capable of use in various other combinations and environments and is capable of changes or modifications within the scope of the inventive concept as expressed herein. Thus, for example, those skilled in the art will recognize, or be able to ascertain, using no more than routine experimentation, numerous equivalents to the specific substances and procedures described herein. Such equivalents are considered to be within the scope of this invention.

EXAMPLE 1

Assay Protocol

The serum from six patients (Table 1) was diluted 1:10 with buffer (PBS, pH 7.4 containing 0.5% BSA and 0.05% Tween 20) and 50 ul of each sample was added to the wells of a microtiter plates coated with food antigens from Milk and Baker's Yeast. Three microtiter plates containing Milk and Yeast antigens were run in parallel for each patient. The diluted samples were added to the plates and incubated overnight then washed 3× with buffer. HRP conjugates were added to the plates as follows: Plate #1-50 ul of anti-Human IgG-HRP @ 1:15,000; Plate #2-50 ul of anti-Human C3d-HRP @ 1:6,000; Plate #3-50 ul of both anti-Human IgG-HRP @ 1:15,000 and anti-Human C3d-HRP @ 1:6,000 (final dilutions). The plates containing the HRP conjugates were incubated for 1 hour at room temperature. The plates were washed 2× with buffer and 200 ul of substrate (OPD, 1 mg/ml in 100 mM Citrate, pH 5.0, 5 ul of $H_2O_2$ per 30 mls) was added and incubated for 20 minutes. The reaction was stopped with 100 ul of 3N $H_2SO_4$ and the absorbance read @ A 492.

TABLE 1

Comparison of anti-Human IgG-HRP, anti-Human C3d-HRP and both anti-Human IgG-HRP and anti-Human CV3d-HRP combined on the relative A492.

| Patient | Plate #1 Milk IgG-HRP | Plate #2 Milk C3d-HRP | Plate #3 Milk IgG/C3d-HRP | Plate #1 Yeast IgG-HRP | Plate #2 Yeast C3d-HRP | Plate #3 Yeast IgG/C3d-HRP |
|---|---|---|---|---|---|---|
| CD, 4/13 | 1.428 | 1.275 | 2.333 | 0.203 | 1.017 | 1.202 |
| JE, 5/13 | 1.076 | 1.501 | 2.379 | 0.105 | 0.120 | 0.246 |
| HW, 5/19 | 0.346 | 0.165 | 0.511 | 0.071 | 0.752 | 0.797 |
| CP, 5/12 | 0.962 | 0.835 | 1.380 | 0.232 | 0.581 | 0.738 |
| GMc, 5/11 | 0.644 | 0.842 | 1.556 | 0.110 | 0.528 | 0.710 |
| GM, 5/6 Control | 0.026 | 0.086 | 0.093 | 0.059 | 0.133 | 0.204 |

EXAMPLE 2

Results and Discussion:

In patient serum samples CD, JE, CP and GMc, the sum of the Milk antigen absorbances for IgG-HRP and C3d-HRP are approximately equal (Milk, Plates #1 and #2) to the absorbance when both IgG/C3d-HRP are used together (Milk, Plate #3). In these patients, if the IgG-HRP (Milk, Plate #1) and C3d-HRP (Milk, Plate #2) absorbances are considered separately, each would be considered positive but the signal increases about two-fold when the IgG/C3d-HRP conjugates are combined and used together (Milk, Plate #3). For example, CD, 4/13 had absorbances of 1.428 and 1.275 for IgG-HRP (Milk, Plate #1) and C3d-HRP (Milk, Plate #2), which when added together, approximate the absorbance of 2.333 for IgG/C3d-HRP (Milk, Plate #3). In one patient, HW (Milk, Plate #2), the sum of the IgG-HRP and C3d-HRP absorbances are actually equal to the absorbance of the IgG/C3d-HRP (Milk, Plate #3) but the relative contribution of the C3d-HRP absorbance (Milk, Plate #2) is very small. Thus, the HW sample would be considered negative if only the C3d-HRP were used alone (Milk, Plate #2). Similarly, in patients CD, JE, CP and GMc the sum of the Yeast antigen absorbances for IgG-HRP (Yeast, Plate #1) and C3d-HRP (Yeast, Plate #2) approximates the absorbance when both IgG/C3d-HRP are used together (Yeast, Plate #3). However, as one can see, the IgG-HRP absorbances (Yeast, Plate #1) are relatively low and would be considered negative if it were not for the contribution of the higher positive absorbances from C3d-HRP (Yeast, Plate #2). Thus, if one used only IgG-HRP (Yeast, Plate #1), CD, JE, HW and GMc samples would be considered negative, when in fact, by using C3d-HRP (Yeast, Plate #2) these samples are positive for IgG-C3d containing immune complexes. GM was negative for both Milk and Yeast antigens and is included as a control. Then net result is that serum "samples", in general, may contain both IgG and immune complexes containing both IgG and C3d. Further, when both IgG and C3d are detected simultaneously, samples that may be negative for either IgG or C3d show up as "positive" rather than "negative" (false negative) when a mixture both IgG and C3d-HRP conjugates is used. Since the use of a mixture both IgG and C3d-HRP conjugates effectively increases the net absorbance, overall assay sensitivity is greatly improved when compared to the sensitivity of the assay when either conjugate is used alone.

What is claimed is:

1. A method of producing a combined signal correlating with a presence of both antigen-specific immunoglobulins and C3d complement fragments in a biological sample comprising:

(a) exposing a solid support comprising an immobilized antigen to the biological sample, wherein said antigen-specific immunoglobulins present in the biological sample are specific to and bind to said immobilized antigen;

(b) washing unbound molecules from the solid support;

(c) exposing said solid support to at least two binding partners: (i) first labeled binding partners comprising first signal-generating labels, wherein the first labeled binding partners specifically bind the antigen-specific immunoglobulins bound to the immobilized antigen; and (ii) second labeled binding partners comprising second signal-generating labels, wherein the second labeled binding partners specifically bind the C3d complement fragments bound to the antigen-specific immunoglobulins bound to the immobilized antigen;

(d) washing unbound first and second labeled binding partners from the solid support; and (e) producing a combined absorbance value from the first signal-generating labels of the first labeled binding partners bound to the solid support and the second signal-generating labels of the second labeled binding partners bound to the solid support;

wherein the first signal-generating labels and the second signal-generating labels are the same, and wherein said combined absorbance value correlates to the presence of antigen-specific immunoglobulins and C3d complement fragments in the biological sample.

2. The method of claim 1 wherein said biological sample is serum or saliva.

3. The method of claim 1 wherein said solid support is a microtiter dish well.

4. The method of claim 1 wherein said second labeled binding partners comprise an anti-C3d antibody which binds to C3d which is bound to antigen-specific immunoglobulins which are bound to the immobilized antigen.

5. The method of claim 1 wherein said second labeled binding partners comprise a horseradish peroxidase (HRP) labeled anti-C3d antibody.

6. The method of claim 1, wherein the first labeled binding partners comprise a human anti-IgG antibody which binds to antigen-specific immunoglobulins which are bound to the immobilized antigen.

7. The method of claim 1, wherein the first labeled binding partners are conjugated to HRP.

8. The method of claim 1 wherein the first labeled binding partners and second labeled binding partners immobilized on the solid support are read quantitatively.

9. The method of claim 1 wherein the antigen is an allergen derived from the group consisting of milk, corn, shrimp, lobster, crab, peanuts, walnuts, fish, eggs, soy and wheat.

10. The method of claim 1 wherein the antigen is an allergen selected from the group consisting of monosodium glutamate (MSG), gluten, casein, and β-lactoglobulin.

11. The method of claim 1 wherein the antigen is casein.

12. The method of claim 1 wherein the antigen is derived from the group consisting of milk, yeast, peanut, and banana.

* * * * *